United States Patent
Wolf, II (10) Patent No.: US 9,901,395 B2
(45) Date of Patent: Feb. 27, 2018

(54) PROBE FOR DIRECTIONAL SURGICAL COAGULATION WITH INTEGRATED NERVE DETECTION AND METHOD OF USE

(71) Applicant: Erich W. Wolf, II, Lake Charles, LA (US)

(72) Inventor: Erich W. Wolf, II, Lake Charles, LA (US)

(*) Notice: Subject to any disclaimer, the term of this patent is extended or adjusted under 35 U.S.C. 154(b) by 1257 days.

(21) Appl. No.: 13/898,193

(22) Filed: May 20, 2013

(65) Prior Publication Data

US 2013/0310830 A1   Nov. 21, 2013

Related U.S. Application Data

(60) Provisional application No. 61/649,701, filed on May 21, 2012, provisional application No. 61/709,442, filed on Oct. 4, 2012.

(51) Int. Cl.

| A61B 18/14 | (2006.01) |
|---|---|
| A61B 5/0492 | (2006.01) |
| A61B 5/00 | (2006.01) |
| A61B 5/04 | (2006.01) |
| A61B 18/00 | (2006.01) |

(52) U.S. Cl.
CPC ........ *A61B 18/1482* (2013.01); *A61B 5/0492* (2013.01); *A61B 5/4836* (2013.01); *A61B 5/04004* (2013.01); *A61B 2018/00589* (2013.01); *A61B 2018/00595* (2013.01); *A61B 2218/002* (2013.01)

(58) Field of Classification Search
CPC . A61B 18/1482; A61B 5/0492; A61B 5/4836; A61B 2018/00589; A61B 2218/002; A61B 2018/00595; A61B 5/04004
See application file for complete search history.

(56) References Cited

U.S. PATENT DOCUMENTS

| 3,845,771 A | 11/1974 | Vise |
| 4,051,855 A | 10/1977 | Schneiderman |
| 4,931,047 A | 6/1990 | Broadwin et al. |
| 5,282,799 A | 2/1994 | Rydell |
| 5,443,463 A * | 8/1995 | Stern ............... A61B 18/14 606/51 |
| 5,796,188 A | 8/1998 | Bays |
| 5,921,923 A * | 7/1999 | Kuck ............... A61B 5/0422 600/373 |
| 6,109,268 A | 8/2000 | Thapliyal et al. |

(Continued)

*Primary Examiner* — Joseph Stoklosa
*Assistant Examiner* — Tigist Demie
(74) *Attorney, Agent, or Firm* — Schultz & Associates, P.C.

(57) ABSTRACT

A cautery apparatus and method are provided that coagulate tissue along a seam and near the ends of the seam. The cautery apparatus and method include a cautery device and an EMG system. When a set of electrodes for the EMG are placed in the lower extremities of a patient, the cautery method injects a current at the cautery device and monitors the EMG electrodes. When nerve stimulation is detected at the EMG electrodes, during tissue coagulation, the position of the cautery device is changed. Generally, the cautery device is repositioned to eliminate nerve stimulation, thereby avoiding nerve damage.

12 Claims, 9 Drawing Sheets

(56) References Cited

U.S. PATENT DOCUMENTS

| | | |
|---|---|---|
| 6,522,904 B1 * | 2/2003 | Mika .................... A61B 5/0492 |
| | | 600/374 |
| 7,041,096 B2 | 5/2006 | Malis et al. |
| 7,306,592 B2 | 12/2007 | Morgan et al. |
| 7,553,307 B2 | 6/2009 | Bleich et al. |
| 7,686,802 B2 | 3/2010 | Stevens-Wright |
| 7,693,562 B2 | 4/2010 | Marino et al. |
| 7,987,001 B2 | 7/2011 | Teichman et al. |
| 8,034,053 B2 | 10/2011 | Whayne et al. |
| 8,083,685 B2 | 12/2011 | Fagin et al. |
| 8,137,284 B2 | 3/2012 | Miles et al. |
| 2003/0069514 A1 * | 4/2003 | Brody .................. A61B 5/0492 |
| | | 600/546 |
| 2008/0065178 A1 | 3/2008 | Kelleher et al. |
| 2010/0152726 A1 | 6/2010 | Cadouri et al. |
| 2010/0160910 A1 | 6/2010 | Kramer et al. |
| 2011/0004207 A1 | 1/2011 | Wallace et al. |
| 2012/0089141 A1 | 4/2012 | Lee et al. |
| 2013/0046292 A1 | 2/2013 | Janssen et al. |

\* cited by examiner

PROBE FOR DIRECTIONAL SURGICAL COAGULATION WITH INTEGRATED NERVE DETECTION AND METHOD OF USE

CROSS-REFERENCE TO RELATED APPLICATIONS

This application claims priority benefit from U.S. Provisional Patent Application No. 61/649,701 filed on May 21, 2012, and U.S. Provisional Patent Application No. 61/709,442 filed on Oct. 4, 2012.

FIELD OF INVENTION

The present invention relates generally to surgical coagulation tools and nerve detection during surgical coagulation.

BACKGROUND

Various surgical tools are available for coagulation or cauterization of tissue. The general, prior art designs include a set of electrodes to which a current is applied. In a monopolar configuration, one electrode is placed against the tissue of interest and the current is returned at a distant electrode. In a bipolar configuration, two local electrodes are placed against the tissue of interest and the current flows between the two electrodes.

Figure 1:
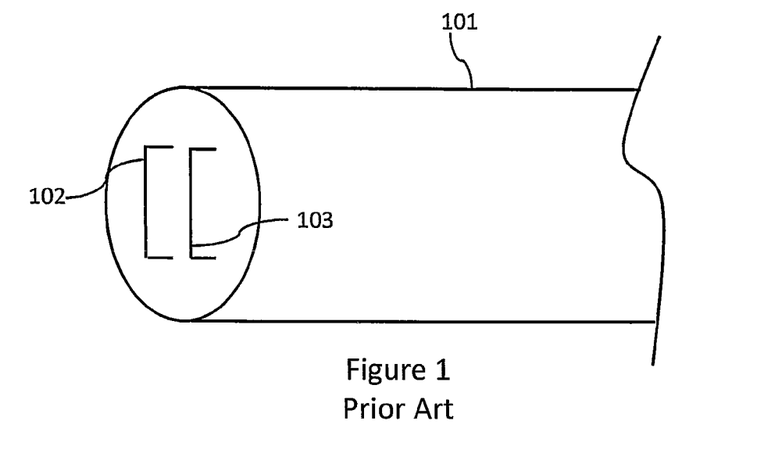
FIG. 1 is a schematic representation of a cauterization probe of the prior art.

Referring to FIG. 1, prior art cautery devices generally require a set of wire frame electrodes at the tip. Cautery probe 101 includes electrode 102 and electrode 103 which are insulated so that electrode 102 and electrode 103 are not in electrical contact.

Figure 2:
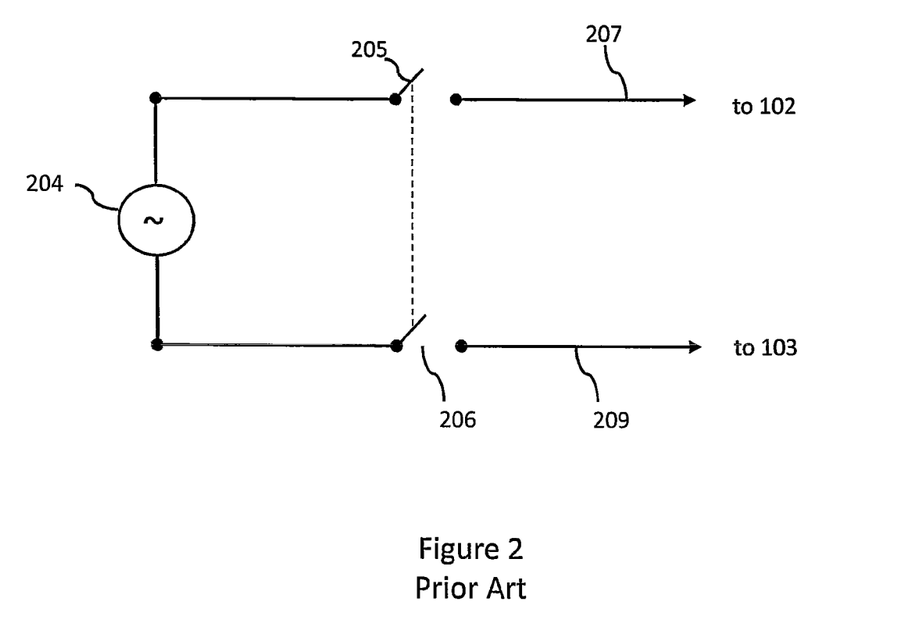
FIG. 2 is a circuit diagram of a cauterization probe of the prior art.

Referring to FIG. 2, switching for a prior art cautery device is shown. Coagulation current source 204 is connected at a first electric potential to switch 205 which is further connected by a conductor 207 to electrode 102. Coagulation current source 204 is connected at a second electric potential to switch 206 which is further connected by a conductor 209 to electrode 103. Switch 205 and switch 206 are SPST (single pole single throw) normally-open switches.

In operation, the prior art cautery device is placed in contact with tissue. Switch 205 and switch 206 are then closed to energize an electric potential difference between electrode 102 and electrode 103. The electric potential difference initiates a current flow from electrode 102 to electrode 103 through the tissue.

U.S. Pat. No. 6,109,268 to Thapliyal et al. discloses an electrosurgical probe that has a tip region which comprises electrode terminals designed to deliver electrical energy in the vicinity of the tip. The return electrodes may comprise a single tubular member of conductive material proximal to the electrode terminals.

U.S. Patent Application Publication No. 2012/0089141 to Lee et al. discloses an electrode body which is flexible and includes a first electrode, an insulator, and a second electrode. A process is disclosed including detecting a nerve responsible for pain and ablation of tissue with electrocautery.

U.S. Pat. No. 7,693,562 to Marino et al. discloses a probe which includes electrodes which may detect an EMG response to detect a nerve.

In U.S. Patent Application Publication No. 2010/0152726 to Cadouri et al., an electrosurgical system with selective control of active and return electrodes is disclosed. The electrosurgical system comprises a wand and a controller. The controller comprises a non-conductive outer surface, at least three electrodes disposed on a distal end of the wand and at least three electrical leads extending from a proximal end of the wand. A control circuit is configured to selectively activate the electrodes.

SUMMARY

Disclosed is a system and method for cauterizing tissue in tightly constrained surgical situations. The system generally includes several electrodes attached to a cautery probe in a unique geometry. Two of the electrodes are co-planar and are of a semicircular shape. The cautery probe also includes annular electrodes adjacent the co-planar electrodes. The arrangement of the probes creates a variable electric field which allows focused cauterization energy that can be changed during use.

The system includes a power source for supplying an electric current to the electrodes through a set of switches. The cautery system can include an automatic controller operatively connected to the set of switches to set them.

In another aspect, the system is provided with an electromyograph connected to the controller to detect nerve responses to the cautery probe. The controller is programmed to determine if a response is received from the electromyograph when the probe is utilized. If a response is received, then the controller causes an alert signal. If a response is not received, then the controller initiates cauterization current flow.

A preferred method is also disclosed. The method provides for iterative energization of a set of current pulses to flow to the electrodes if a response signal is not received from the electromyograph within a predetermined time period.

In another aspect, the method additionally provides the cautery probe with a controller responsive to the electromyograph. The controller is configured in an idle state wherein the first electrode and the second electrode are not energized. The controller is then configured in a test state which iteratively energizes the set of current pulses and determines if the response signal is received from the electromyograph within a predetermined time from the beginning of each iteration. If the response signal is received within the predetermined time, then the method continues by iteratively energizing the set of current pulses and determining if the response signal is received. If the response signal is not received within the predetermined time, then the method continues by energizing the coagulation current.

BRIEF DESCRIPTION OF DRAWINGS

The disclosed inventions will be described with reference to the following drawings.

DETAILED DESCRIPTION

Figure 3:
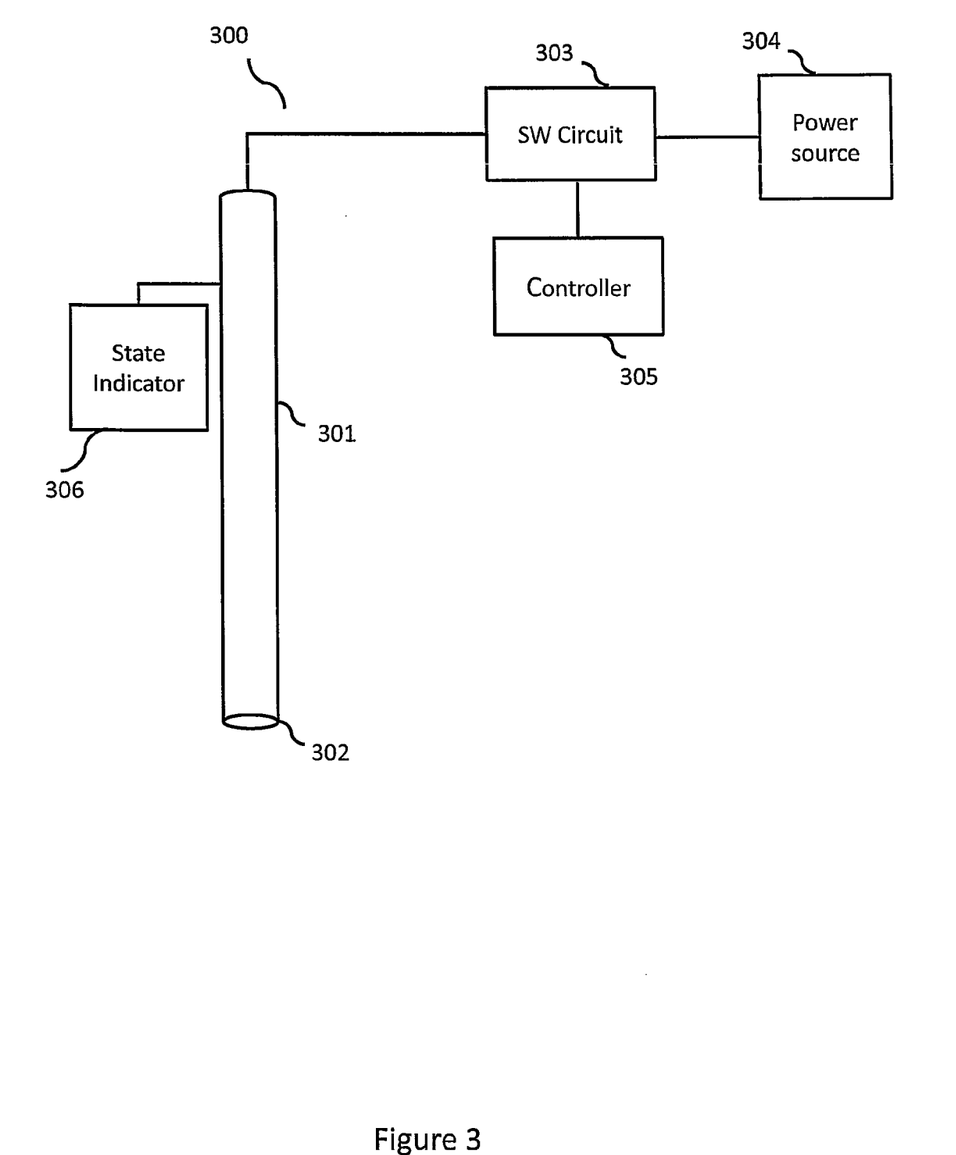
FIG. 3 is a schematic representation of a preferred embodiment of the cautery system.

Referring to FIG. 3, a block diagram of a preferred embodiment of a cautery system is described. Cautery system 300 includes a cautery probe 301 for coagulating tissue, a switching circuit 303 connected to cautery probe 301, a power source 304 connected to switching circuit 303 for powering the cautery probe and controller 305 for controlling the switching circuit 303.

In one embodiment, controller 305 is a mechanical control such as a resilient button connected to a switch. In another embodiment, controller 305 is an electronic controller. The switch states are set by applying an electrical signal through the electronic controller.

Cautery probe 301 further comprises a state indicator 306. State indicator 306 is provided in the cautery system to indicate an operational state as selected by controller 305. State indicator 306 is any device or combination of devices configured to alert a user of the system state. For example, state indicator 306 is configured to control a set of indicator LEDs or a piezoelectric speaker for generation of an audible tone.

In a preferred embodiment, the cautery probe can include a housing or handle encapsulating the switch, the control and the state indicator connected by a set of wires to an external power source. In another embodiment, the switch, the control, the state indicator and the power source are housed separately from the cautery probe.

In other preferred embodiments, controller 305 may be implemented entirely in hardware, entirely in software (including firmware, resident software, micro-code, etc.) or combining software and hardware implementation that may all generally be referred to herein as a "circuit," "module," "component," or "system." Further, aspects of the present disclosure may take the form of a computer program product embodied in one or more computer readable media having computer readable program code embodied thereon.

Any combination of one or more computer readable media may be utilized. The computer readable media may be a computer readable signal medium or a computer readable storage medium. For example, a computer readable storage medium may be, but not limited to, an electronic, magnetic, optical, electromagnetic, or semiconductor system, apparatus, or device, or any suitable combination of the foregoing. More specific examples of the computer readable storage medium would include, but are not limited to: a portable computer diskette, a hard disk, a random access memory ("RAM"), a read-only memory ("ROM"), an erasable programmable read-only memory ("EPROM" or Flash memory), an appropriate optical fiber with a repeater, a portable compact disc read-only memory ("CD-ROM"), an optical storage device, a magnetic storage device, or any suitable combination of the foregoing. Thus, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. The propagated data signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, or any suitable combination thereof.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages.

Aspects of the present disclosure are described herein with reference to flowchart illustrations and/or block diagrams of methods, systems and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

Figure 4:
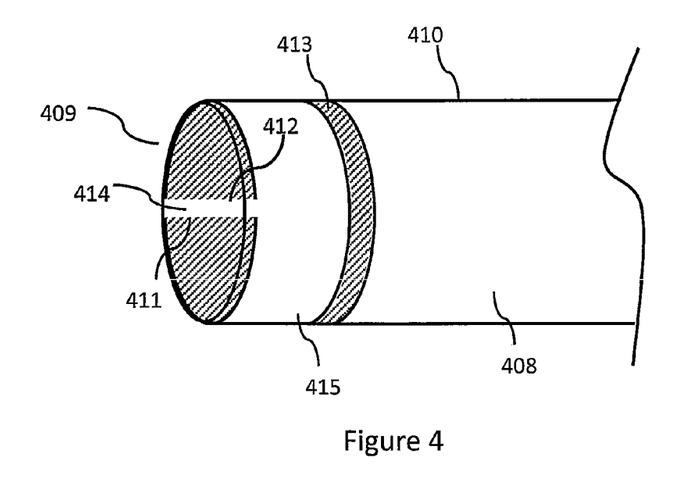
FIG. 4 is a perspective view of a preferred embodiment of a cautery device.

Referring to FIG. 4, a first embodiment is shown. Cautery probe 410 is comprised of an elongated shaft 408 made of a disposable rigid plastic such as Dacron®, Teflon®, or polyvinyl chloride. More durable materials may be employed such as porcelain and other non-conductive ceramic materials. Stainless steel may also be employed for the shaft, but the electrodes must be insulated from the shaft. Cautery probe 410 includes three electrodes disposed on distal end surface 409. Electrode 411 and electrode 412 are each a semicircular "D" configuration. In the preferred embodiment, the electrodes are diametrically opposed, and set in the same plane, generally perpendicular to the longitudinal axis of the probe. In another preferred embodiment, the electrodes are set in the same plane; but, the plane is set at an oblique angle, such as 30°, 45°, 60°, to the longitudinal axis of the probe. Each of the electrodes is composed of polished stainless steel, embedded in the distal end of the probe during manufacture. Alternatively, the electrodes can be affixed with an epoxy adhesive.

Ring electrode 413 is disposed on radial surface of shaft 408. Ring electrode 413 is located adjacent to and proximate electrodes 411 and 412 and forms an annular band surrounding the probe. In a preferred embodiment, the ring electrode is made of polished stainless steel and is embedded in the surface of the probe.

Electrodes 411 and 412 are separated from each other by insulating gap 414. Ring electrode 413 is separated from electrodes 411 and 412 by insulating gap 415. Gaps 414 and 415 serve to insulate electrodes 411, 412 and ring electrode 413 from one another and from shaft 408.

Figure 5:
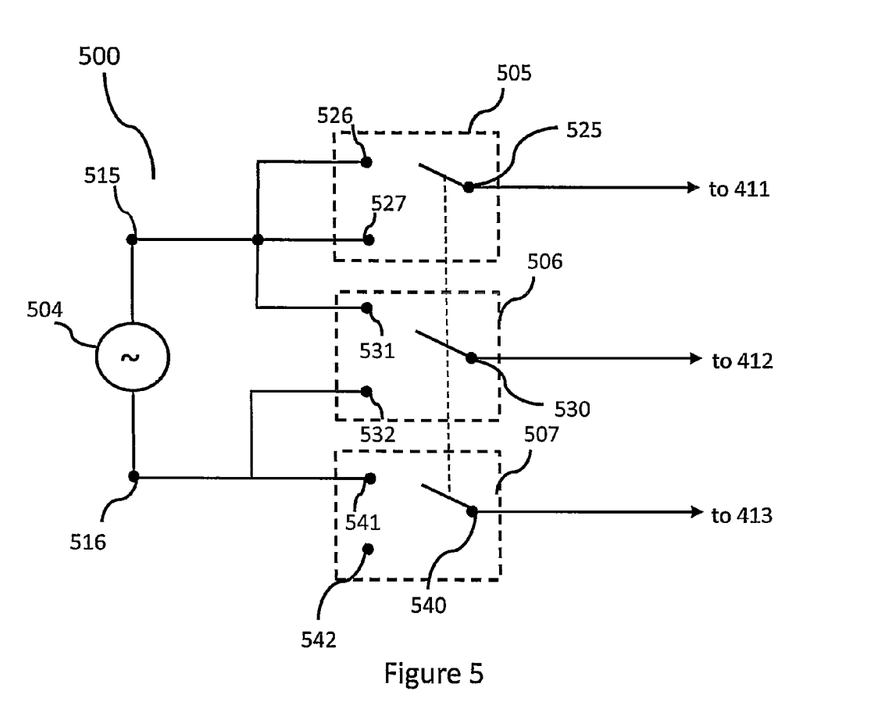
FIG. 5 is a circuit diagram of a preferred embodiment of a switching circuit for a cautery device.

Referring to FIG. 5, switching circuit 500 is disclosed. Switching circuit 500 employs three SPDT (single pole double throw) normally-open switches, switch 505, switch 506 and switch 507. Power supply 504, connected to switching circuit 500, supplies an electric current across power terminals 515 and 516. In another preferred embodiment, the three SPDT switches are operable as momentary switches in one of several fixed states. In a preferred embodiment, the three SPDT switches are transistor based relays responding to the controller. In an alternate embodiment the three SPDT switches are mechanical.

Switch 505 includes terminal 525 connected to electrode 411, terminal 526 connected to terminal 531 of switch 506 and terminal 527 connected to power terminal 515. Terminal 526 is further connected to power terminal 515. In a first position of switch 505, terminal 525 is connected to terminal 526. In a second position of switch 505, terminal 525 is connected to terminal 527.

Switch 506 includes terminal 530 connected to electrode 412, terminal 531 connected to terminal 526 of switch 505 and terminal 532 connected to power terminal 516. In a first position of switch 506, terminal 530 is connected to terminal 531. In a second position of switch 506, terminal 530 is connected to terminal 532.

Switch 507 includes terminal 540 connected to ring electrode 413, terminal 541 connected to power terminal 516, and floating terminal 542 which is normally unconnected. In a first position of switch 507, terminal 540 is connected to terminal 541. In a second position of switch 507, terminal 540 is connected to floating terminal 542.

In a preferred embodiment, there are two selectable modes of instantaneous operation, "tip" mode and "ring" mode.

To enable the "tip" mode, terminal 525 is connected to terminal 527, terminal 530 is connected to terminal 532 and terminal 540 is connected to floating terminal 542, thereby sending current across electrodes 411 and 412. Alternatively, terminal 507 can be left in its normally open state. In the "tip" mode, tissue is cauterized between electrodes 411 and 412.

To enable the "ring" mode, terminal 525 is connected to terminal 526, terminal 530 is connected to terminal 531 and terminal 540 is connected to terminal 541 thereby connecting electrodes 411 and 412 together to power terminal 515 and connecting ring electrode 413 to power terminal 516. The "ring" mode results in a current across ring electrode 413 and electrodes 411 and 412. In the "ring" mode tissue is cauterized at the side of the cautery probe, between ring electrode 413 and either electrode 411 or electrode 412.

Figure 6:
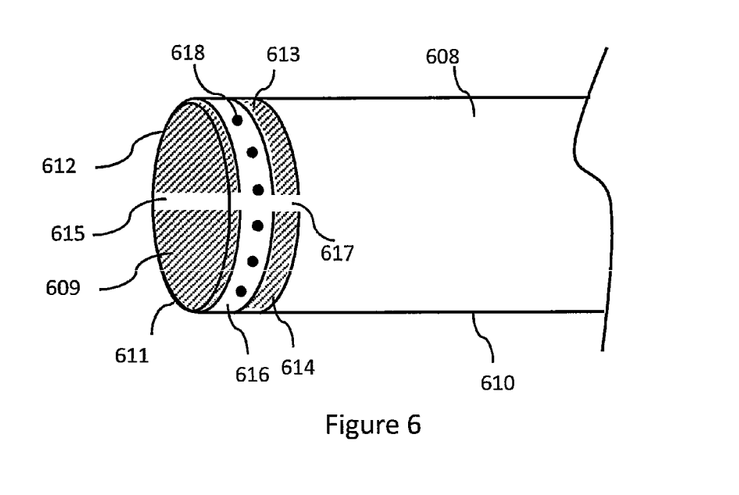
FIG. 6 is a perspective view of an alternate embodiment of a cautery device.

Referring to FIG. 6, a second preferred embodiment is described. Cautery probe 610 is comprised of an elongated shaft 608 made of a disposable rigid plastic such as Dacron®, Teflon®, or polyvinyl chloride. More durable materials may be employed such as porcelain and other non-conductive ceramic materials. Stainless steel may also be employed for the shaft, but the electrodes must be insulated from the shaft. Shaft 608 has a generally cylindrical surface and distal end 609. Electrode 611 and electrode 612 are disposed on distal end 609. Electrode 611 and electrode 612 are semicircular "D" shaped and are diametrically opposed from each other. Electrode 611 and electrode 612 are co-planar and are generally perpendicular to the longitudinal axis of the shaft. Electrode 613 is disposed on shaft 608 adjacent electrode 612. Electrode 614 is disposed on the shaft 608 adjacent to electrode 609. Each electrode 613 and 614 is semi-annular. The electrodes are diametrically opposed. Holes 618 are provided for a supply of irrigation fluid.

Electrodes 611 and 612 are insulated from each other by gap 615. Electrodes 613 and 614 are electrically insulated from electrodes 611 and 612 by gap 616 and from each other by gap 617 and a similar gap (not shown) diametrically opposed to gap 617.

Figure 7:
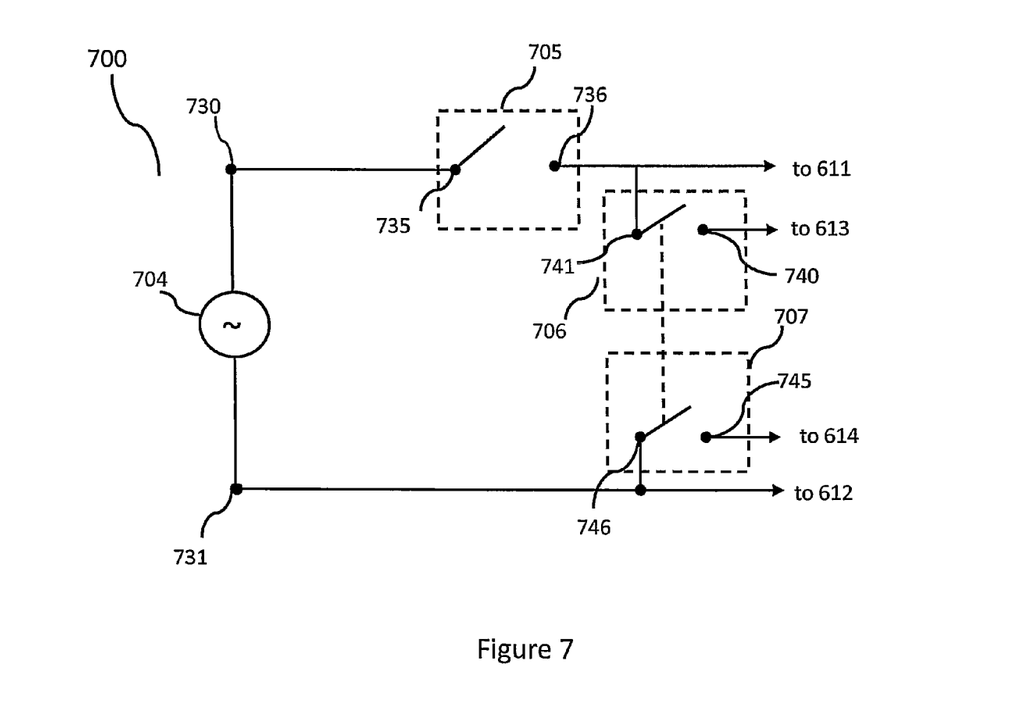
FIG. 7 is a circuit diagram of an alternate embodiment of a switching circuit for a cautery device.

Referring to FIG. 7, a preferred embodiment of switching circuit 700 is described. Switching circuit 700 employs three SPST (single pole single throw) normally-open switches, switch 705, switch 706 and switch 707. Power source 704, connected to switching circuit 700, supplies an electric potential difference across power terminals 730 and 731. In a preferred embodiment, the switches are mechanical momentary switches. Switches 706 and 707 may be configured to open and close in tandem.

In an alternate embodiment, the switches are transistor based relays operated by the controller. In one embodiment, all switches are capable of independent closure. In another embodiment, switches 706 and 707 are mechanically linked and close and open at the same time.

Switch 705 includes terminal 735 connects to terminal 730 and terminal 736 to electrode 611. Electrode 612 is directly connected to power terminal 731. Switch 706 connects terminal 740 to electrode 613 and terminal 741 to terminal 736.

Switch 707 connects terminal 745 to electrode 614 and terminal 746 connected to electrode 612.

When switch 705 is closed, electric current is supplied to electrode 611 and terminal 741 of switch 706 and returned through electrode 612. In the open state of switch 705, no electric current flows through any of the electrodes 611, 612, 613 or 614.

In the closed state of switch 706, electrode 611 is connected to electrode 613 and electric current is allowed to flow from power source 704 to electrode 613 based on the state of switch 705. In the open state of switch 706 no electric current flows to electrode 613.

In the closed state of switch 707, electrode 612 is connected to electrode 614 and electric current is allowed to return to power source 704 from electrode 614 based on the state of switch 705. In the open state of switch 707 no electric current is returned from electrode 614.

The selectable modes offer different cauterization field patterns that are related to the geometry of the tip and are novel and highly useful in certain surgical situations. For example, when only switch 705 is closed, a "tip" mode is created in which a field is provided directly ahead and perpendicular to the shaft. The mode is useful in cauterizing vessels as the tip is pressed against them longitudinally, preventing blood flow. When switches 705 and 706 are closed simultaneously, a cauterization field is produced which is biased toward the tip and the right side of the end of the probe. This mode is called the "tip right" mode. It is useful in tight surgical situations where cauterization must occur beside the probe but reorientation is not possible. In a similar way, when switches 705 and 707 are closed, a field is produced that is biased toward the tip and the left side of the probe. This mode is called the "tip left" mode.

Finally, when switch 705, 706, and 707 are closed simultaneously the probe is placed in "side" mode. In side mode, coagulation can occur circumferentially at the side of the probe tip, perpendicular to the long-axis of probe 608. This mode is useful in situations where coagulation is desired on the side-wall of a tightly constrained surgical filed.

Figure 8:
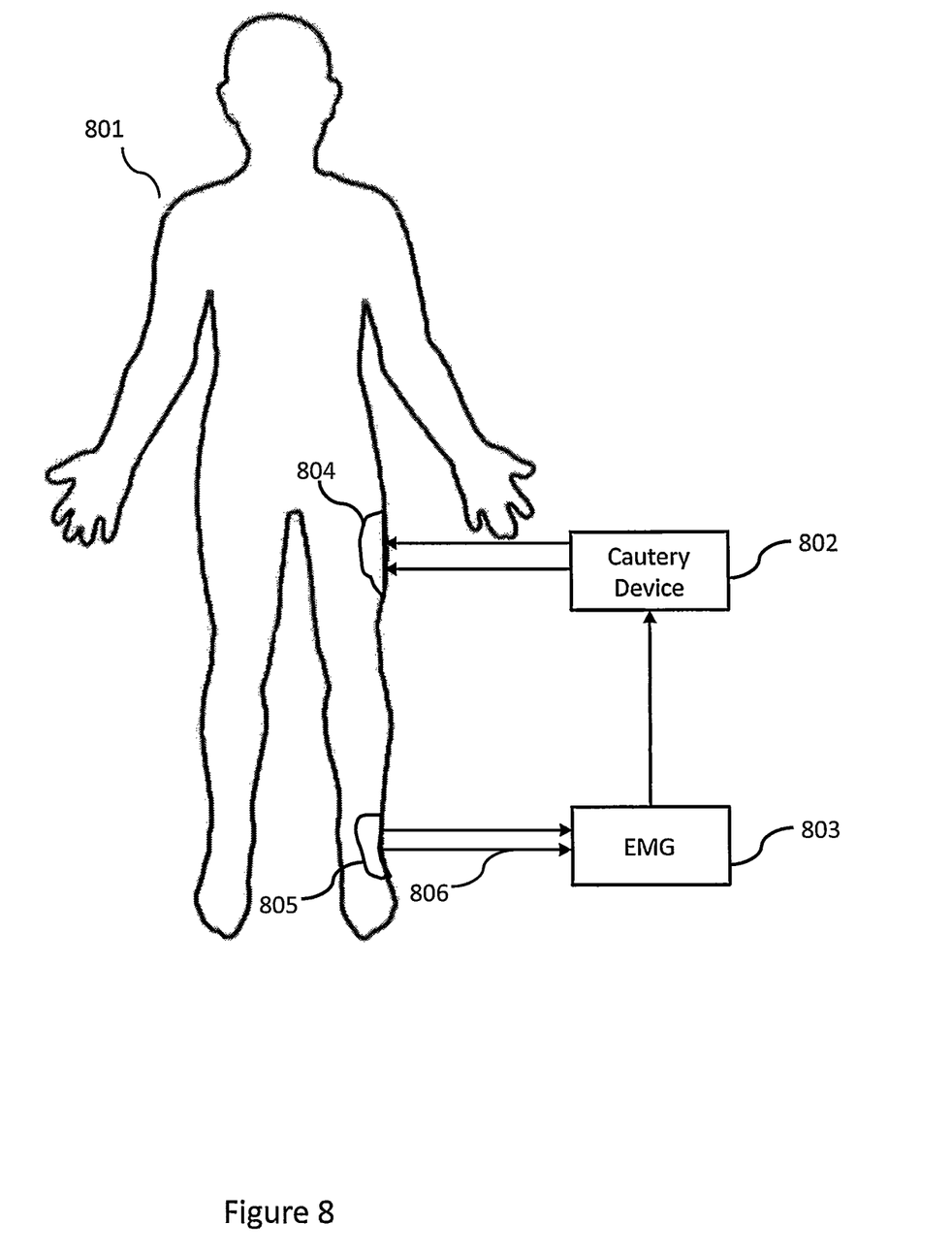
FIG. 8 is a block diagram depicting a system for nerve detection during coagulation using a preferred embodiment of the cautery device.

Referring to FIG. 8, a block diagram of a combined cautery and nerve detection system is shown. In a preferred embodiment, a cautery device 802 is applied to cauterize and coagulate a wound area 804 on patient 801. A set of EMG electrodes 806 is connected to another area 805 of patient 801 and further connected to an electromyograph system 803 for detecting nerve activity. Electromyograph system 803 is also in communication with cautery device 802. The presence of an electromyograph provides an opportunity for nerve detection to reduce or eliminate the possibility of inadvertent nerve damage during coagulation.

Figure 9:
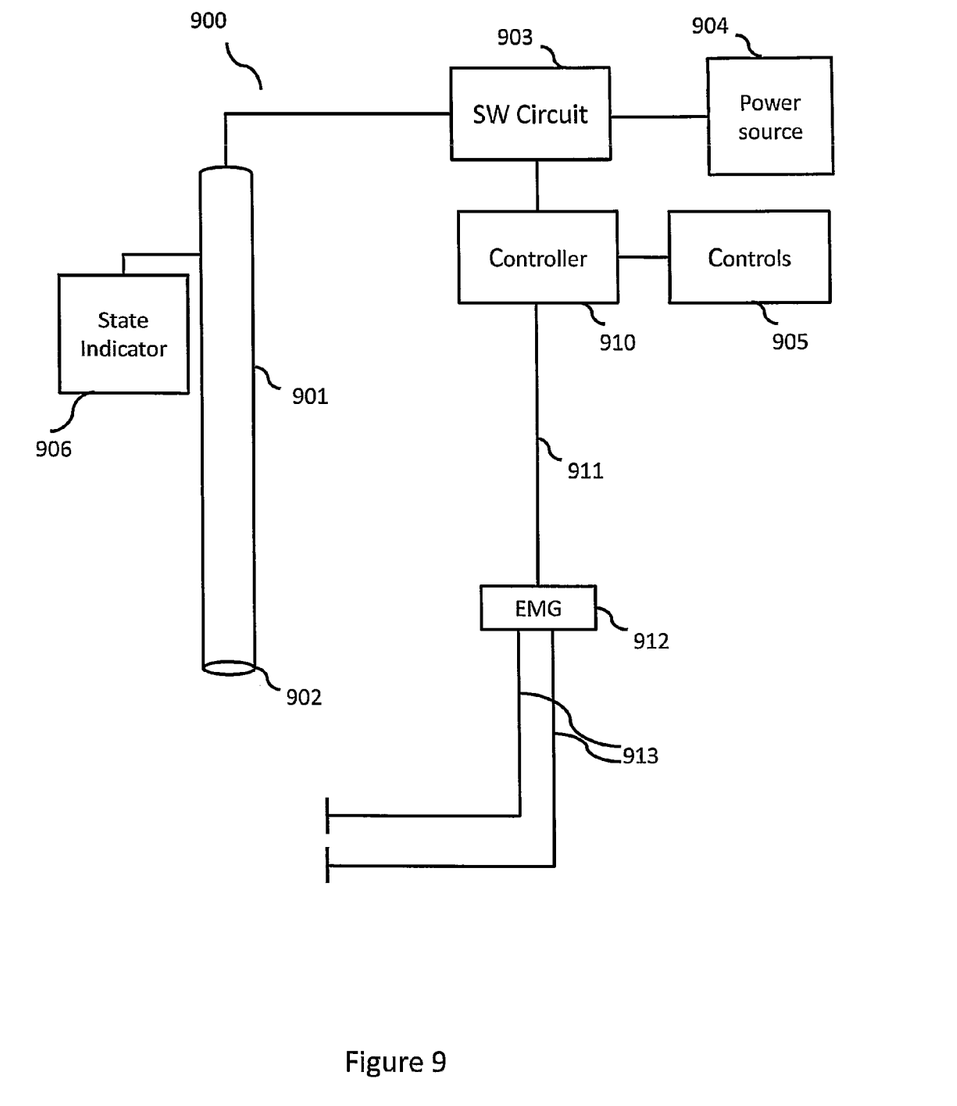
FIG. 9 is a schematic representation of a preferred embodiment of a cautery device including an integrated electromyograph.

Referring to FIG. 9, a detailed diagram of a preferred embodiment of the combined cautery and nerve detection system is described. Combined system 900 includes a cautery probe 901 having a set of electrodes 902 and a state indicator 906, a switching circuit 903 connected to cautery probe 901, a power source 904 connected to switching circuit 903 for powering the cautery probe, a controller 910 for automatically controlling the state of the switching circuit and for communications with electromyograph system 912 and a control 905 for user interaction with the combined system.

Combined system 900 further comprises electromyograph system 912 having a set of EMG electrodes 913 for placement at a known responsive area of a patient. Electromyograph system 912 and set of EMG electrodes 913 are configured to detect electrical response to nerve excitations in the vicinity of a tissue surface interacting with the cautery probe. Electromyograph system 912 is in communication with controller 910 over a link 911 to indicate detection of the nerve excitations.

Control 905 is provided to change the state of switching circuit 903 thereby changing the system state. Control 905, for example, can be as simple as an on/off button or include a set of buttons. Additionally, state indicator 906 is provided to indicate a system state.

In a preferred embodiment, set of electrodes 902 comprise a set of end electrodes and a set of ring electrodes, as previously disclosed.

In a preferred embodiment, controller 910 comprises a processor, such as a microcontroller, and memory. However, controller 910 can be any electrical circuit capable of changing the state of the switching circuit and responding to communications from the electromyograph system, such as a digital state machine. For example, controller 910 can be a discrete electronic circuit or a programmable logic device such as an ASIC or FPGA.

State indicator 906 is any device or combination of devices configured to alert a user of the system state. For example, state indicator 906 is configured to control a set of indicator LEDs or an auditory speaker.

Link 911 is any communications link compatible with electromyograph system 912. In one example, link 911 can be a proprietary wired or optical connection. In another example, link 911 can be a wireless connection such as a Bluetooth link.

In another embodiment, controller 910 and switching circuit 903 are combined as a single circuit.

Figure 10:
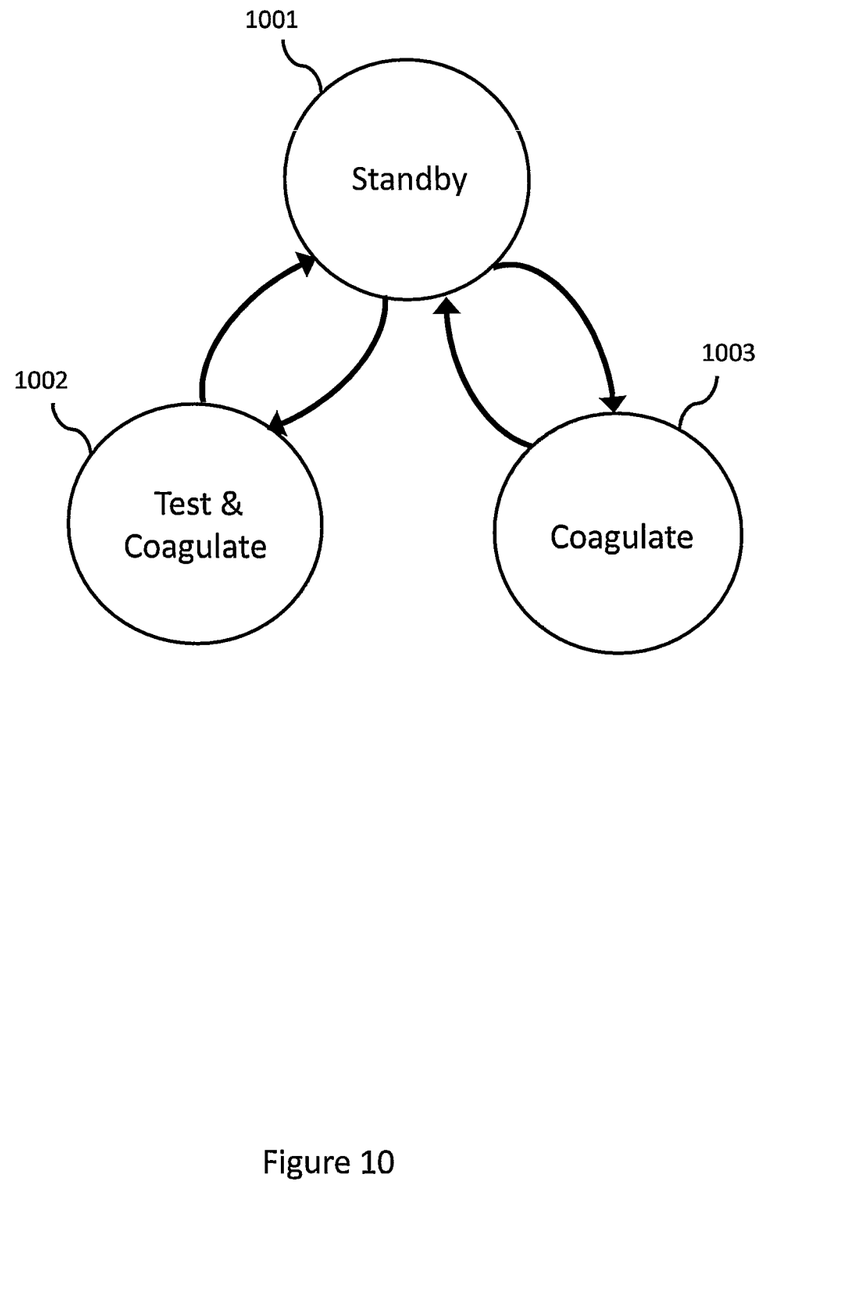
FIG. 10 is device state diagram for a preferred embodiment of a preferred embodiment of a cautery device including an integrated electromyograph.

Referring to FIG. 10, a state diagram for the combined cautery and nerve detection system is disclosed. The cautery system begins in a "standby" state 1001 until moved into the "coagulate" mode 1003 or into a "test and coagulate" mode 1002. In "coagulate" mode 1003, cauterization current is applied to the desired electrodes as long as the set of switches is actuated by the control. In "test and coagulate" mode 1002, the set of switches are momentarily actuated to issue a test pulse to the coagulation electrodes. An absence of electromyographic response is awaited from the electromyographic system prior to energizing the coagulation current. Coagulation current is withheld if there is synchronous nerve activity detected. If no nerve activity is detected then the coagulation current is applied for a specified duration until another test pulse is delivered or the user returns the system to standby state 1001.

In use, the system states are traversed by depressing or releasing the various switches. For example, a user presses a switch to cause the test pulse and manually await the electromyographic response. The user then applies the coagulation current if no nerve activity is detected.

Figure 11:
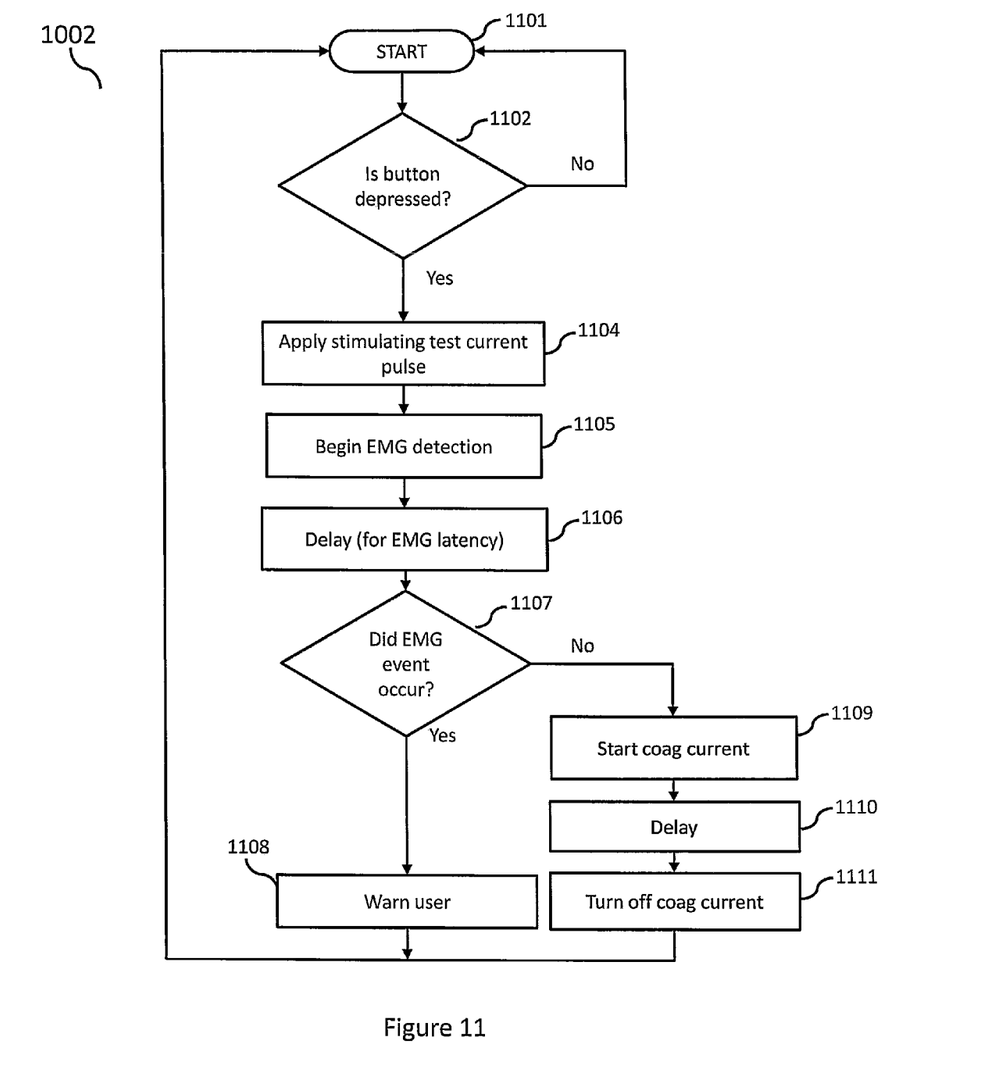
FIG. 11 is a flow diagram for a preferred embodiment of a method for testing and coagulation.

FIG. 11 shows a flowchart for the "test and coagulate" mode 1002. At step 1101, the control is operated, for example, by depressing a momentary button switch. At step 1102, the controller checks the switch for a closed condition. If the switch is open, then the system returns to standby state 1001. If the switch is closed, then the method moves to step 1104. At step 1104, a stimulating current pulse is sent through electrodes 411 and 412, for tip mode or electrodes 411, 412, and 413 for side mode, or alternatively, electrodes 611 and 612 for tip mode or electrodes 611, 612, 613 and 614 for side mode. At step 1105, electromyograph is signaled to start detection. Step 1106 implements a time delay after the electromyograph is signaled. In the preferred embodiment, the time delay is about 100 ms. The time delay may be varied. At step 1107, the electromyograph is queried for detection of nerve activity.

If nerve activity is detected, then at step 1108, a warning message is sent and the method returns to step 1101. The warning message can be, for example, a light activated by the state indicator or a warning sound emitted from a speaker.

If nerve activity is not detected, then at step 1109, the cautery device energizes coagulation current from at least one of the "tip" mode and the "ring" mode as selected by the control. Step 1110 implements a time delay. At step 1111, the coagulation current is turned off and the method repeats at step 1102 for a different position of the cautery device.

At step 1109, the state indicator can be additionally programmed to indicate that coagulation occurs, for example, by activating a light or by emitting a sound.

Figure 12:
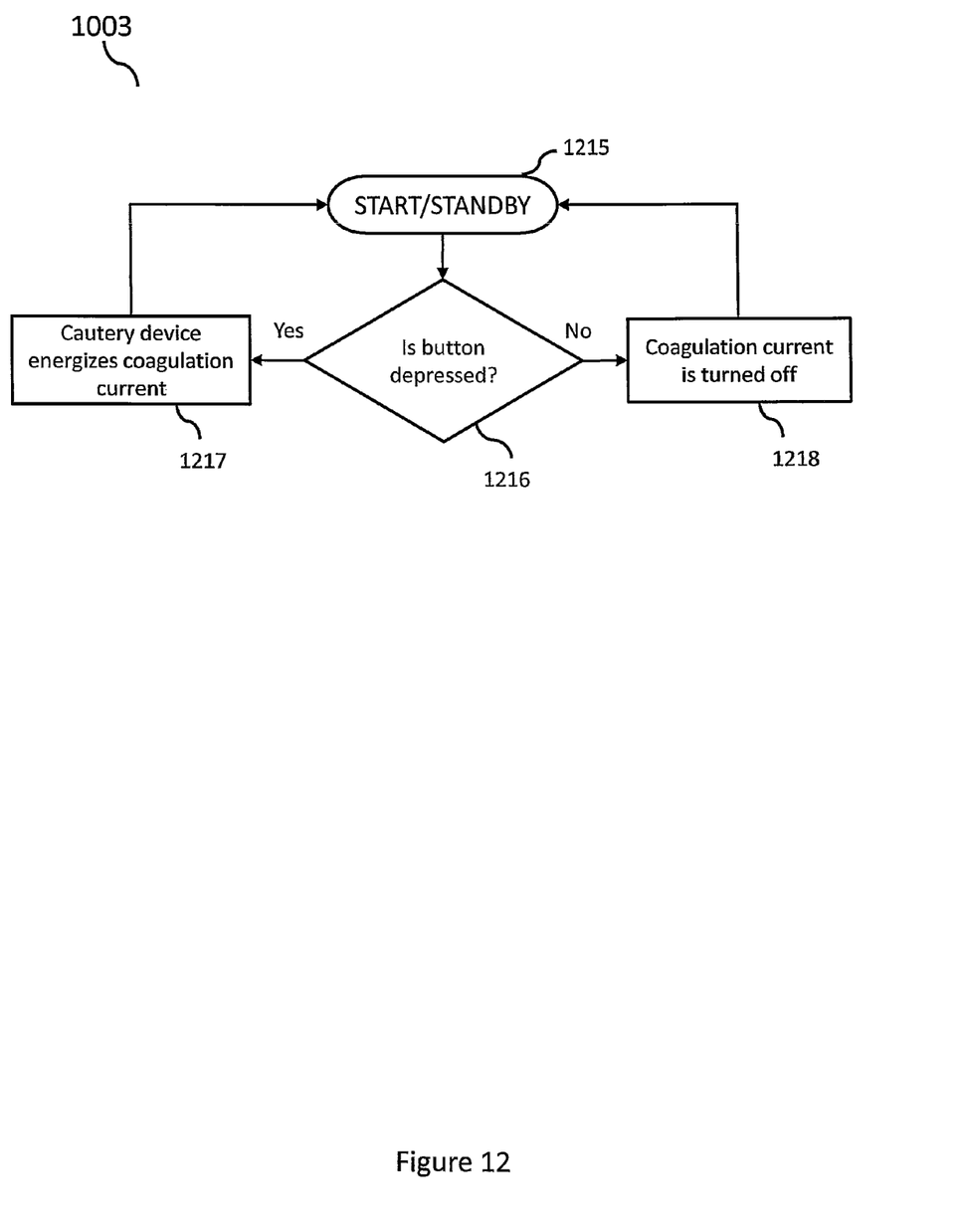
FIG. 12 is a flow diagram for a preferred embodiment of a method for coagulation.

FIG. 12 demonstrates a flow chart for the "coagulate" mode 1003. At step 1215, the "coagulate" mode is started when the control is operated, for example, a button switch is depressed. At step 1216, the controller determines if the corresponding switch is still closed. If the switch is closed, then at step 1217, the cautery device energizes coagulation current "tip" mode or the "side" mode as selected by the control. The method repeats at step 1216. If the switch is released and open, then in step 1218, the coagulation current is turned off. The system then returns to step 1215.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed and limited only by the scope and spirit of the claims now appended hereto.

The invention claimed is:

1. A cautery system comprising:
a probe;
a first planar semicircular electrode, attached to the probe;
a second planar semicircular electrode, attached to the probe, adjacent and diametrically opposed to the first planar, semicircular electrode;
an annular electrode, attached to the probe, adjacent the first planar semicircular electrode and the second planar semicircular electrode;
a power source;
a set of switches attached to the first planar semicircular electrode, the second planar semicircular electrode, the annular electrode and the power source;
the set of switches, when configured in a first state, connecting the power source to the first planar semicircular electrode and the second planar semicircular electrode;
the set of switches, when configured in a second state, connecting the power source to the first planar semicircular electrode, the second planar semicircular electrode and the annular electrode; and,
wherein the first planar semicircular electrode is flat and resides entirely in a distal plane;
wherein the second planar semicircular electrode is flat and resides entirely in the distal plane;
wherein the distal plane is generally perpendicular to a longitudinal axis of the probe.

2. The cautery system of claim 1 wherein the power source supplies an electric potential difference between a first power terminal and a second power terminal and, the set of switches further comprises:
a first switch comprising a first terminal connected to the first electrode, a second terminal connected to the first power terminal, and a third terminal;
a second switch comprising a fourth terminal connected to the second electrode, a fifth terminal connected to the second power terminal, and a sixth terminal connected to the third terminal; and,
a third switch comprising a seventh terminal connected to the third electrode and an eighth terminal connected to the second power terminal.

3. The cautery system of claim 2 wherein:
the first state is established when the first terminal is connected to the second terminal, the fourth terminal is connected to the fifth terminal and the third switch is in a normally open position; and,
the second state is established when the first terminal is connected to the third terminal, the fourth terminal is connected to the sixth terminal and the seventh terminal is connected to the eighth terminal.

4. The cautery system of claim 3 further comprising a controller operatively connected to the set of switches to place the set of switches in one of the group of the first state and the second state.

5. The cautery system of claim 4 further comprising:
an electromyograph operatively connected to the controller; and,
the controller selectively configured to operate the set of switches in a test mode.

6. The cautery system of claim 5 wherein the controller is further configured to:
receive a signal from the electromyograph; and
send a first alert signal in response to the signal.

7. The cautery system of claim 6 wherein the controller is further configured to place the set of switches in the first state if the signal is not received from the electromyograph within a predetermined time.

8. The cautery system of claim 6 wherein the controller is further configured to place the set of switches in the second state if the signal is not received from the electromyograph within a predetermined time.

9. The cautery system of claim 1 wherein the probe is further comprised of a disposable plastic.

10. The cautery system of claim 1 further comprising:
a non-conductive linear channel, formed between the first planar semicircular electrode and the second planar semicircular electrode, in the distal plane.

11. A cautery system comprising:
a probe;
a first planar semicircular electrode, attached to the probe;
a second planar semicircular electrode, attached to the probe, adjacent and diametrically opposed to the first planar, semicircular electrode;
an annular electrode, attached to the probe, adjacent the first planar semicircular electrode and the second planar semicircular electrode;
a power source;
a set of switches attached to the first planar semicircular electrode, the second planar semicircular electrode, the annular electrode and the power source;
the set of switches, when configured in a first state, connecting the power source to the first planar semicircular electrode and the second planar semicircular electrode;
the set of switches, when configured in a second state, connecting the power source to the first planar semicircular electrode, the second planar semicircular electrode and the annular electrode; and,
wherein the first planar semicircular electrode is flat and resides entirely in a distal plane;
wherein the second planar semicircular electrode is flat and resides entirely in the distal plane;
wherein the distal plane is set at an oblique angle to a longitudinal axis of the probe.

12. The cautery system of claim 11 further comprising:
the distal plane set at the oblique angle to the longitudinal axis of the probe, the oblique angle being one of the group of 30 degrees, 45 degrees, and 90 degrees.

* * * * *